United States Patent
Hammann et al.

(10) Patent No.: US 10,456,172 B2
(45) Date of Patent: Oct. 29, 2019

(54) MAGNETICALLY ACTUATEABLE ROD INSERTION FOR MINIMALLY INVASIVE SURGERY

(71) Applicant: NUVASIVE, INC., San Diego, CA (US)

(72) Inventors: Conrad Tyler Hammann, San Diego, CA (US); Derek Matteo, San Diego, CA (US); Matthew Tobias Jacobs, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 88 days.

(21) Appl. No.: 15/432,631

(22) Filed: Feb. 14, 2017

(65) Prior Publication Data
US 2017/0231663 A1 Aug. 17, 2017

Related U.S. Application Data

(63) Continuation of application No. PCT/US2017/017693, filed on Feb. 13, 2017.

(60) Provisional application No. 62/295,001, filed on Feb. 12, 2016.

(51) Int. Cl.
*A61B 17/70* (2006.01)
*A61B 17/00* (2006.01)

(52) U.S. Cl.
CPC ........... *A61B 17/7016* (2013.01); *A61B 2017/00876* (2013.01); *A61B 2017/00991* (2013.01)

(58) Field of Classification Search
CPC .................................. A61B 17/7002–7017
See application file for complete search history.

(56) References Cited

U.S. PATENT DOCUMENTS

| | | |
|---|---|---|
| 5,180,393 A | 1/1993 | Commarmond |
| 5,375,823 A | 12/1994 | Navas |
| 5,387,213 A | 2/1995 | Breard |
| 5,628,756 A | 5/1997 | Barker, Jr. |
| 5,672,175 A | 9/1997 | Martin |
| RE36,221 E | 6/1999 | Breard |
| 6,296,643 B1 | 10/2001 | Hopf |
| 6,530,929 B1 | 3/2003 | Foley |
| 7,160,300 B2 | 1/2007 | Jackson |
| 7,179,261 B2 | 2/2007 | Sicvol |
| 7,250,052 B2 | 7/2007 | Landry |
| 7,377,921 B2 | 5/2008 | Studer |
| 7,491,208 B2 | 2/2009 | Pond, Jr. |

(Continued)

FOREIGN PATENT DOCUMENTS

| | | |
|---|---|---|
| CN | 202776519 | 3/2013 |
| WO | WO2007/014119 | 2/2007 |

(Continued)

OTHER PUBLICATIONS

International Search Report dated Aug. 17, 2017 for International Application No. PCT/US2017/017693, 5 pages.

(Continued)

*Primary Examiner* — Jacqueline T Johanas (57) ABSTRACT

The present disclosure describes a spinal fixation system comprising a telescoping spinal rod, as well as methods of its use and a guide tower for use therewith. The telescoping rod can be extended after it has been inserted into the patient below the fascia, which permits it to be extended in the sub-fascial space.

21 Claims, 5 Drawing Sheets

(56) References Cited

U.S. PATENT DOCUMENTS

| | | |
|---|---|---|
| 7,758,617 B2 | 7/2010 | Iott |
| 7,815,663 B2 | 10/2010 | Trieu |
| 7,976,546 B2 | 7/2011 | Geist |
| 8,057,472 B2 | 11/2011 | Walker |
| 8,092,461 B2 | 1/2012 | Geist |
| 8,197,490 B2 | 6/2012 | Pool |
| 8,317,801 B2 | 11/2012 | Geist |
| 8,333,771 B2 | 12/2012 | Geist |
| 8,337,528 B2 | 12/2012 | Ferree |
| 8,343,192 B2 | 1/2013 | Kiester |
| 8,366,715 B2 | 2/2013 | Geist |
| 8,382,756 B2 | 2/2013 | Pool |
| 8,419,734 B2 | 4/2013 | Walker |
| 8,419,773 B2 | 4/2013 | Biedermann |
| 8,449,543 B2 | 5/2013 | Pool |
| 8,523,922 B2 | 9/2013 | May |
| 8,617,214 B2 | 12/2013 | Malek |
| 8,685,026 B2 | 4/2014 | Carls |
| 8,715,159 B2 | 5/2014 | Pool |
| 8,734,488 B2 | 5/2014 | Pool |
| 8,852,187 B2 | 10/2014 | Pool |
| 8,852,236 B2 | 10/2014 | Kiester |
| RE45,436 E | 3/2015 | Geist |
| 8,974,463 B2 | 3/2015 | Pool |
| 9,011,499 B1 | 4/2015 | Kiester |
| RE45,659 E | 9/2015 | Geist |
| 9,179,938 B2 | 11/2015 | Pool |
| 9,179,960 B2 | 11/2015 | Walker |
| 9,186,183 B2 | 11/2015 | Pool |
| 9,198,755 B2 | 12/2015 | Shaolian |
| 9,339,309 B1 | 5/2016 | Geist |
| RE46,096 E | 8/2016 | Geist |
| RE46,282 E | 1/2017 | Geist |
| 9,757,159 B2 | 9/2017 | Pool |
| 9,770,274 B2 | 9/2017 | Pool |
| 9,848,914 B2 | 12/2017 | Pool |
| 2006/0036259 A1* | 2/2006 | Carl ................. A61B 17/70 606/90 |
| 2007/0043359 A1* | 2/2007 | Altarac ............. A61B 17/025 606/86 A |
| 2007/0191846 A1* | 8/2007 | Bruneau .......... A61B 17/7004 606/86 A |
| 2007/0239159 A1 | 10/2007 | Altarac |
| 2010/0217271 A1 | 8/2010 | Pool |
| 2010/0249856 A1* | 9/2010 | Iott ................... A61B 17/7085 606/86 A |
| 2010/0280553 A1* | 11/2010 | Bruneau .......... A61B 17/7004 606/259 |
| 2011/0196435 A1 | 8/2011 | Forsell |
| 2012/0109202 A1 | 5/2012 | Kretzer |
| 2012/0130428 A1 | 5/2012 | Hunziker |
| 2012/0271353 A1 | 10/2012 | Barry |
| 2013/0072983 A1 | 3/2013 | Lindquist |
| 2013/0123854 A1 | 5/2013 | Kondrashov |
| 2013/0218207 A1 | 8/2013 | Carls |
| 2013/0338713 A1* | 12/2013 | Kawakami ........ A61B 17/7014 606/258 |
| 2013/0338714 A1 | 12/2013 | Chang |
| 2014/0100613 A1* | 4/2014 | Iott ................... A61B 17/7074 606/279 |
| 2014/0194932 A1* | 7/2014 | Bruneau .......... A61B 17/7004 606/258 |
| 2014/0236234 A1 | 8/2014 | Kroll |
| 2014/0296918 A1 | 10/2014 | Fening |
| 2016/0270825 A1* | 9/2016 | Wentz .............. A61B 17/7016 |

FOREIGN PATENT DOCUMENTS

| | | |
|---|---|---|
| WO | WO2010/030651 | 3/2010 |
| WO | WO2016/134326 | 8/2016 |

OTHER PUBLICATIONS

Written Opinion of the International Searching Authority dated Aug. 17, 2017 for International Application No. PCT/US2017/017693, 15 pages.

* cited by examiner

MAGNETICALLY ACTUATEABLE ROD INSERTION FOR MINIMALLY INVASIVE SURGERY

CROSS-REFERENCE TO RELATED APPLICATIONS

This application is a continuation of International Application PCT/US17/17693, filed 13 Feb. 2017 (pending). International Application PCT/US17/17693 cites the priority of U.S. Patent Application No. 62/295,001, filed on 12 Feb. 2016. The contents of both of the foregoing applications are incorporated by reference herein in their entireties.

BACKGROUND

Field

The present disclosure relates generally to medical devices, and specifically to surgical instruments and methods for performing spinal procedures.

Background

The spine is critical in human physiology for mobility, support, and balance. The spine protects the nerves of the spinal cord, which convey commands from the brain to the rest of the body, and convey sensory information from the nerves below the neck to the brain. Even minor spinal injuries can be debilitating to the patient, and major spinal injuries can be catastrophic. The loss of the ability to bear weight or permit flexibility can immobilize the patient. Even in less severe cases, small irregularities in the spine can put pressure on the nerves connected to the spinal cord, causing devastating pain and loss of coordination.

The spinal column is a bio-mechanical structure composed primarily of ligaments, muscles, bones, and connective tissue that forms a series of vertebral bodies stacked one atop the other and intervertebral discs between each vertebral body. The spinal column provides support to the body and provides for the transfer of the weight and the bending movements of the head, trunk and arms to the pelvis and legs; complex physiological motion between these parts; and protection of the spinal cord and the nerve roots.

The stabilization of the vertebra and the treatment for spinal conditions is often aided by a surgically implanted fixation device which holds the vertebral bodies in proper alignment and reduces the patient's pain and prevents neurologic loss of function. Spinal fixation is a well-known and frequently used medical procedure. Spinal fixation systems are often surgically implanted into a patient to aid in the stabilization of a damaged spine or to aid in the correction of other spinal deformities. Existing systems often use a combination of rods, plates, pedicle screws, bone hooks, locking screw assemblies, and connectors, for fixing the system to the affected vertebrae. The system components may be rigidly locked together to fix the connected vertebrae relative to each other, stabilizing the spine until the bones can fuse together.

A spinal rod is often anchored to two or more vertebrae to immobilize the spine between the two vertebrae. To reduce tissue trauma and opportunity for infection, there have been attempts to develop minimally invasive approaches. Sometimes, minimally invasive rod insertion includes advancing the rod towards the anchors through a guide and then angling a rod inserter to rotate the rod to a position that is in line with the rod channels in the anchors. Because of the limited space available to maneuver the rod, the longer the rod is the more challenging the insertion becomes. This creates two problems. The awkwardness in guiding a rod of sufficient length to connect the desired vertebrae can result in errors, such as passing the rod above the fascia. It also results in limiting the lengths of the rod that can be inserted in a minimally invasive manner.

Consequently there is a need in the art for a way to insert longer rods below the patient's fascia in a minimally invasive manner.

SUMMARY

The present disclosure describes a spinal fixation system comprising a telescoping spinal rod, as well as methods of its use and a guide tower for use therewith. The telescoping rod can be extended after it has been inserted into the patient below the fascia, which permits it to be extended in the sub-fascial space.

In a first aspect, a system for spinal fixation is provided, the system comprising: a bone anchor including a distal bone fastener member, a proximal rod housing comprising a rod channel; and a telescoping spinal rod dimensioned to fit within the rod channel, the telescoping spinal rod having an extended configuration and a collapsed configuration, wherein the telescoping spinal rod has a first longitudinal length in the collapsed configuration and a second longitudinal length in the extended configuration, and wherein the first longitudinal length is less than the distance between a vertebral pedicle in a subject and an adjacent vertebral pedicle in the subject.

In a second aspect, a system for spinal fixation is provided, the system comprising: a bone anchor including a bone fastener member, a first rod housing comprising a first rod channel, and a second rod housing comprising a second rod channel; a first telescoping spinal rod positioned within the first rod channel, the first telescoping spinal rod having an extended configuration and a collapsed configuration; and a second telescoping spinal rod positioned within the second rod channel, the second telescoping spinal rod having an extended configuration and a collapsed configuration; wherein the first telescoping spinal rod and second telescoping spinal rod extend in opposite directions from the bone anchor.

In a third aspect, a guide tower assembly for guiding a spinal rod into position from a first bone anchor to a second bone anchor is provided, the guide tower assembly comprising: an elongate tower member having a proximal end, a distal end, and a longitudinal axis; a lumen running from the proximal end to the distal end of the elongate tower member; a longitudinal slot in the elongate tower member that connects to the lumen; a bone anchor engagement member at the distal end of the tower member configured to reversibly fasten the elongate tower member to a rod housing of the first bone anchor; a first rod holder having a first rod engagement feature at a distal end of the rod holder and a first translating shaft connected to the first rod engagement feature, wherein the first translating shaft is capable of translating relative to the elongate tower member parallel to the longitudinal axis of the elongate tower member, and wherein the first rod engagement feature translates with the first translating shaft; a second rod holder having a second rod engagement feature at a distal end of the second rod holder and a second translating shaft connected to the second engagement feature, wherein the second translating shaft is capable of translating relative to the elongate tower member parallel to the longitudinal axis of the elongate tower member, wherein the second rod engagement feature translates with the second translating shaft and wherein the second translating shaft is capable of translating at a different velocity than a velocity of translation of the first translating shaft.

In a fourth aspect, a method of fixating a first vertebra to a second vertebra is provided, comprising: fastening a first bone anchor to the first vertebra; fastening a second bone anchor to a second vertebra; inserting a telescoping spinal rod into the first bone anchor in a collapsed configuration, the telescoping spinal rod having an extended configuration and the collapsed configuration, wherein the telescoping spinal rod has a collapsed length that is shorter than a length between the first bone anchor and the second bone anchor, and an extended length that is no shorter than the length between the first bone anchor and the second bone anchor; extending the telescoping spinal rod from the collapsed to the extended configuration, to cause the telescoping spinal rod to extend into the second bone anchor; locking the telescoping spinal rod in position in the first bone anchor; and locking the telescoping spinal rod in position in the second bone anchor.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

DETAILED DESCRIPTION

Illustrative embodiments of a system for spinal fixation, parts, and methods for use thereof, are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The system for spinal fixation, parts, and methods for use thereof disclosed herein boasts a variety of inventive features and components that warrant patent protection, both individually and in combination.

A system for spinal fixation 5 is provided, useful for minimally invasive approaches. In a general embodiment shown in FIG. 1, the system comprises a bone anchor 10 and a telescoping spinal rod 15 configured to be fastened to the bone anchor 10. The telescoping rod 15 is capable of assuming an extended configuration and a collapsed configuration. Embodiments of the telescoping rod 15 may also be capable of assuming intermediate configurations, in which the rod 15 is neither maximally extended nor maximally collapsed. In the collapsed configuration the rod 15 has a first longitudinal length, and in the extended configuration it has a second longitudinal length that is longer than the first longitudinal length. The first (collapsed) longitudinal length is less than the distance between a vertebral pedicle in a subject and an adjacent vertebral pedicle in the subject. The second (extended) longitudinal length is at least the distance between a vertebral pedicle in a subject and an adjacent vertebral pedicle in the subject. Thus, when extended, the rod is capable of connecting two adjacent pedicles.

Figure 1:
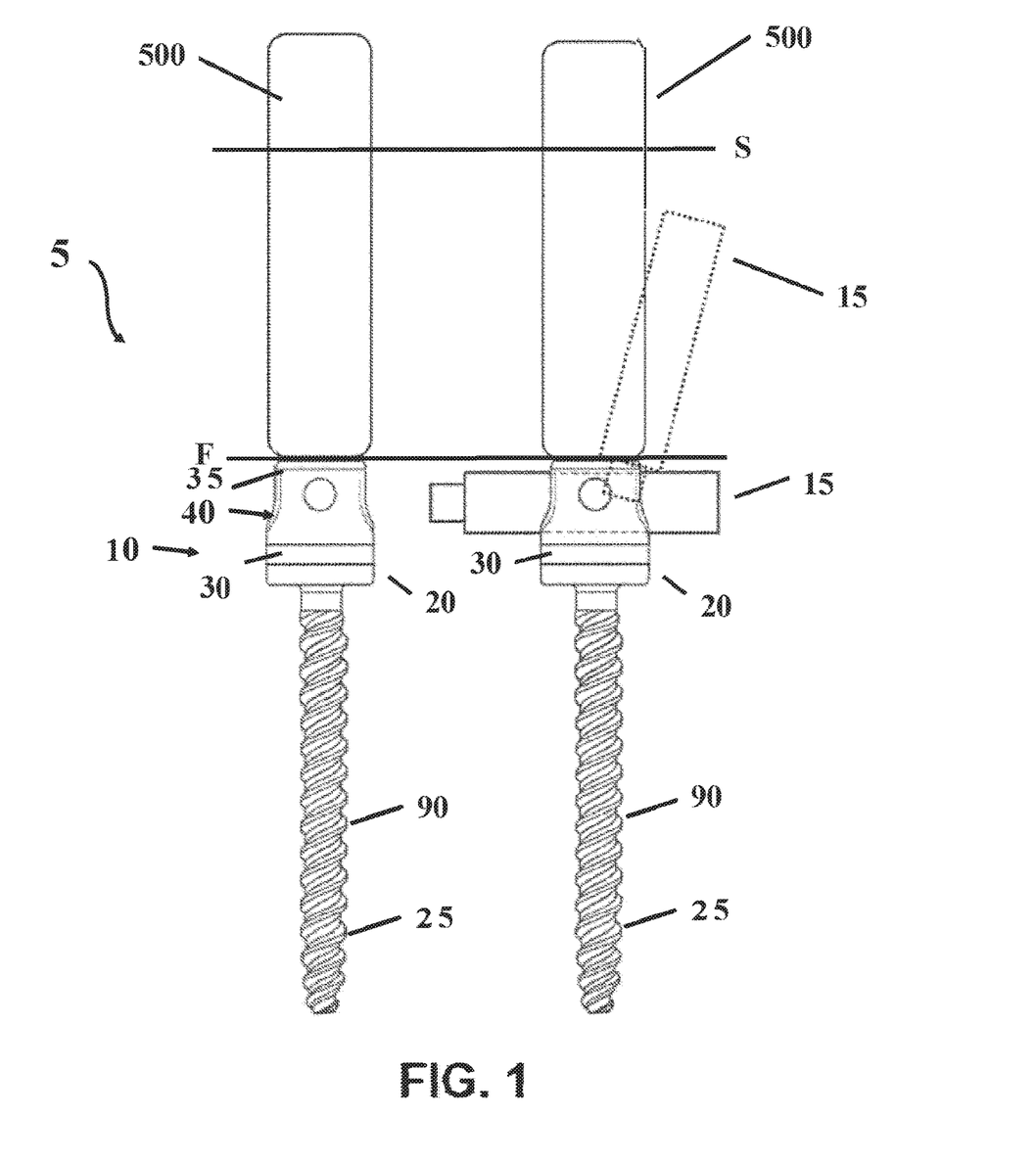
FIG. 1. A side view of an embodiment of the system for spinal fixation, showing a telescoping spinal rod seated in the rod channel of a bone anchor while in its retracted position. The skin (S) and fascia (F) of the subject are shown.
Figure 2:
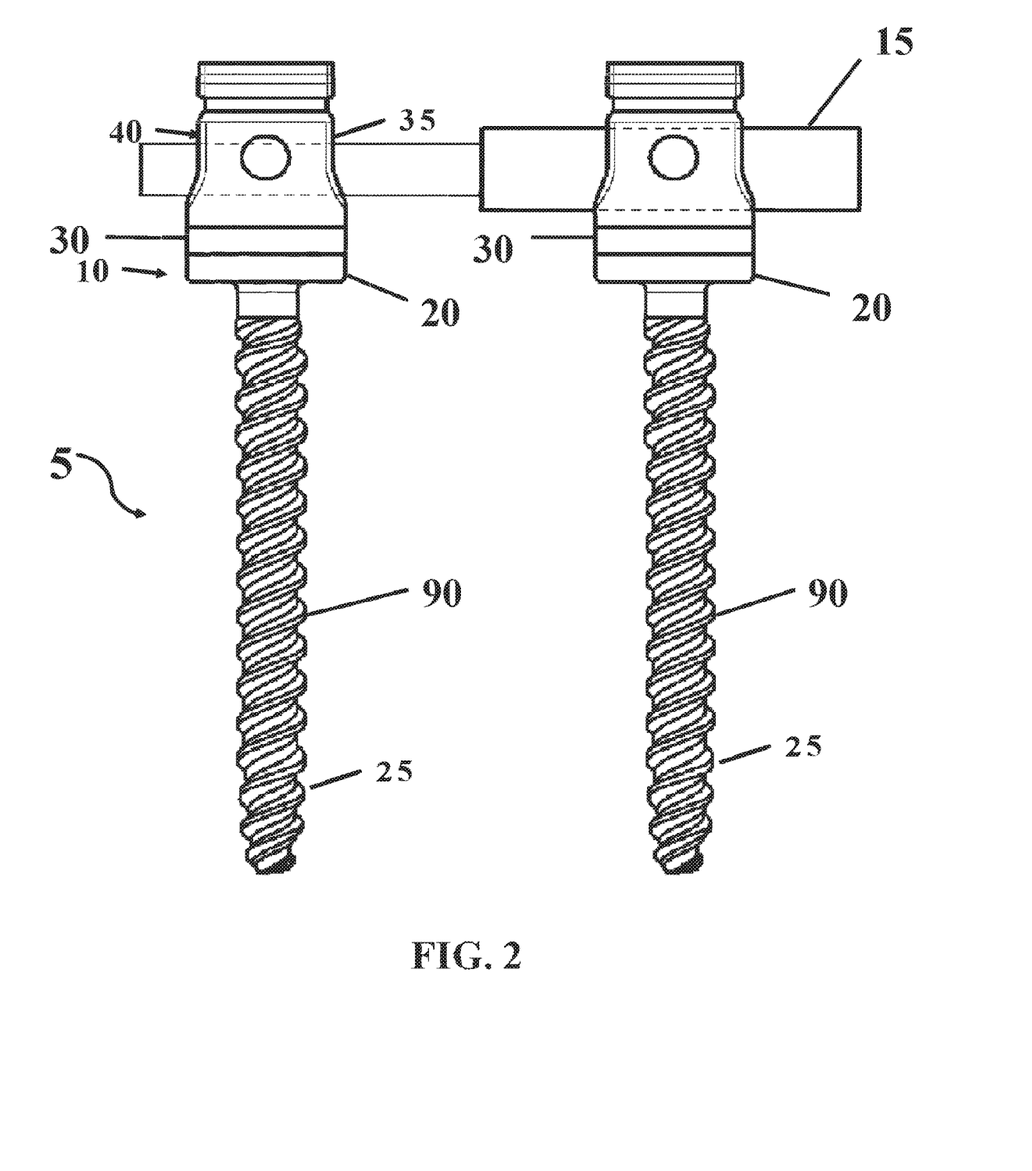
FIG. 2. A side view of an embodiment of the system for spinal fixation, showing a telescoping spinal rod seated in the rod channel of a bone anchor while in its expanded position.

The bone anchor 10 functions to limit the movement of the rod 15 relative to the vertebra. Such bone anchors 10 include bone screws, ties, hooks, and other such anchors as known in the art. In a specific embodiment the bone anchor 10 is a pedicle screw 20. The pedicle screw 20 comprises a distal bone screw 25 fastened to a proximal rod housing 30. The rod housing 30 may be of the "tulip" type, having two arms 35 extending proximally to form a rod channel 40 in between. Such tulips typically have helical flanges or screw threads on the interior surface, to allow a fixation screw to be inserted to reduce and lock the position of a spinal rod, once it is seated in the rod channel. The pedicle screw 20 may not allow relative movement between the bone screw 25 and the rod housing 30, or it may allow deflection of the rod housing 30 relative to the bone screw 25. The deflection may occur about exactly one axis (uniaxial) or it may occur about multiple axes (multiaxial). In a specific embodiment the rod housing 30 swivels relative to the bone screw 25 like a universal joint.

As shown in FIG. 1, one or more guide assemblies 500 may be used with the system. Such a guide assembly may comprise an elongate tower member having a proximal end, a distal end, and a longitudinal axis; a lumen running from the proximal end to the distal end of the elongate tower member; a longitudinal slot in the elongate tower member that connects to the lumen; and a bone anchor engagement member at the distal end of the tower member configured to reversibly fasten the elongate tower member to a rod housing of the first bone anchor. The rod is inserted into the guide tower assembly and translated distally though the lumen and longitudinal slot, with or without the assistance of an inserter. The guide assemblies 500 can be reversibly fastened to the bone anchors by minimally invasive techniques. The short length of the rod on insertion (in its retracted configuration) limits the back angle necessary to rotate the rod, which makes it easier to get under the subject's fascia and keep the incision small. The rod is then extended once it is positioned in the rod housing.

Some embodiments of the system 5 are configured to allow the telescoping rod to be inserted towards the first bone anchor with the rod axis generally parallel to the guide assembly. The rod is then reoriented to a position with the rod axis generally perpendicular to the guide assembly prior to adjusting the rod to the extended position, the distal end of the rod passing through the longitudinal slot and underneath the fascia.

Some embodiments of the telescoping spinal rod 15 are configured to elongate and contract upon receipt of a remote signal. Such embodiments have the advantage of allowing the rod 15 to be modified in length during a procedure without inserting an additional instrument into the patient. Such embodiments of the rod 15 also have the advantage of allowing the rod 15 to be modified in length postoperatively without an invasive procedure. The remote signal may be an electromagnetic signal, such as a rotating magnetic field. A specific mechanism for transforming a rotating magnetic field into extension or contraction of the spinal rod 15 is a magnet operatively coupled to the rod ("rod magnet") 45 configured to rotate in the presence of the rotating magnetic field, which in turn causes the rod 15 to elongate or contract. Whether the rod 15 elongates or contracts may depend on the direction of the magnetic field's rotation. The rod magnet 45 will be composed of a magnetic material, such as a ferromagnetic material.

Figure 3:
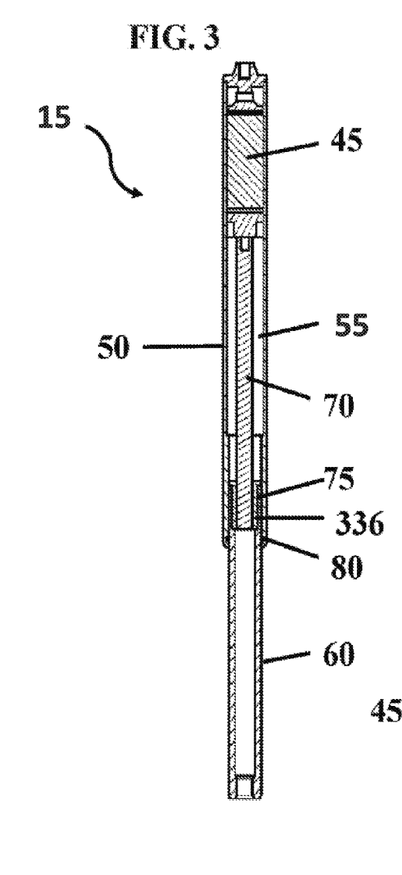
FIG. 3. A cross-sectional side view of an embodiment of the telescoping spinal rod.

A specific embodiment of the telescoping spinal rod 15 is shown in FIG. 3. As shown, the telescoping spinal rod 15 comprises: a first elongate element containing a cavity 55; a second elongate element 60 dimensioned to at least partially fit within the cavity 55, and having an internally threaded region 65; and a lead screw 70 coupled to rotate when the rod magnet 45 rotates, and comprising an externally threaded region 75 engaged to the internally threaded region 65 of the second elongate element 60, such that rotation of the lead screw 70 causes the second elongate element 60 to translate relative to the first elongate element 50. In this embodiment the rod magnet 45 rotates about approximately the longitudinal axis of the telescoping rod 15, and directly drives the rotation of the lead screw 70. The lead screw's 70 rotation in turn causes longitudinal translation of the second elongate element 60, causing it to either extend from or contract into the first elongate element 50. A dynamic seal 80 may advantageously be present at the interface between the first 50 and second 60 elongate elements to prevent intrusion of fluids into the interior of the rod 15.

Alternatively, the rod 15 may be configured such that the rod magnet 45 indirectly drives the rotation of the lead screw 70, for example through a gear train. The use of a gear train has the advantage of allowing an unequal ratio between the angular motion of the rod magnet 45 and the angular motion of the lead screw 70. For example, if the gear ratio is less than 1:1 (screw 70:magnet 45), then delicate changes in the length of the rod 15 may be accomplished, and increased torque may be realized with less force. On the other hand, if the gear ratio is greater than 1:1, the length of the telescoping rod 15 may be modulated at greater speeds with less torque.

An alternative embodiment of the system 5 employs a bone anchor 10 with two rod housings, to allow two telescoping rods 15 to be fastened to the bone anchor 10. The two rods 15 are configured to telescope in different directions. This allows rods to be extended from the first vertebra to two adjacent vertebra (one cranial to the first vertebra and one caudal to the first vertebra) through the same small incision. The alternative embodiment of the system comprises a bone anchor including a bone fastener member, a first rod housing comprising a first rod channel, and a second rod housing comprising a second rod channel; a first telescoping spinal rod positioned within the first rod channel, the first telescoping spinal rod having an extended configuration and a collapsed configuration; and a second telescoping spinal rod positioned within the second rod channel, the second telescoping spinal rod having an extended configuration and a collapsed configuration; wherein the first telescoping spinal rod and second telescoping spinal rod extend in opposite directions from the bone anchor. One or both of the telescoping rods may have any structure or properties that are disclosed as suitable for the telescoping rod 15 in the unidirectional system described above.

Figure 6:
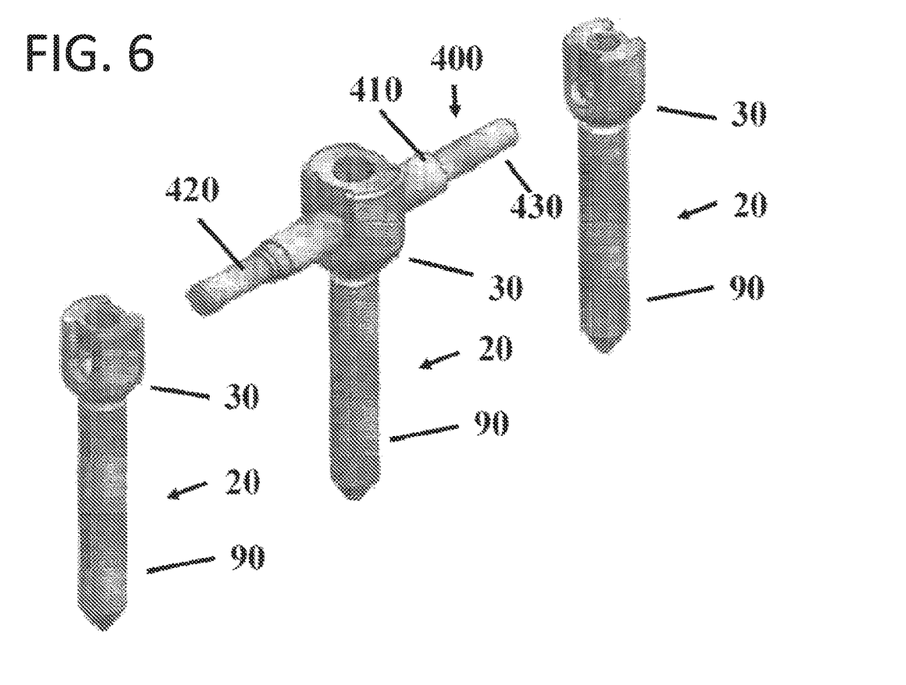
FIG. 6. An embodiment of the system for spinal fixation with a bidirectional telescoping rod in the retracted position.
Figure 7:
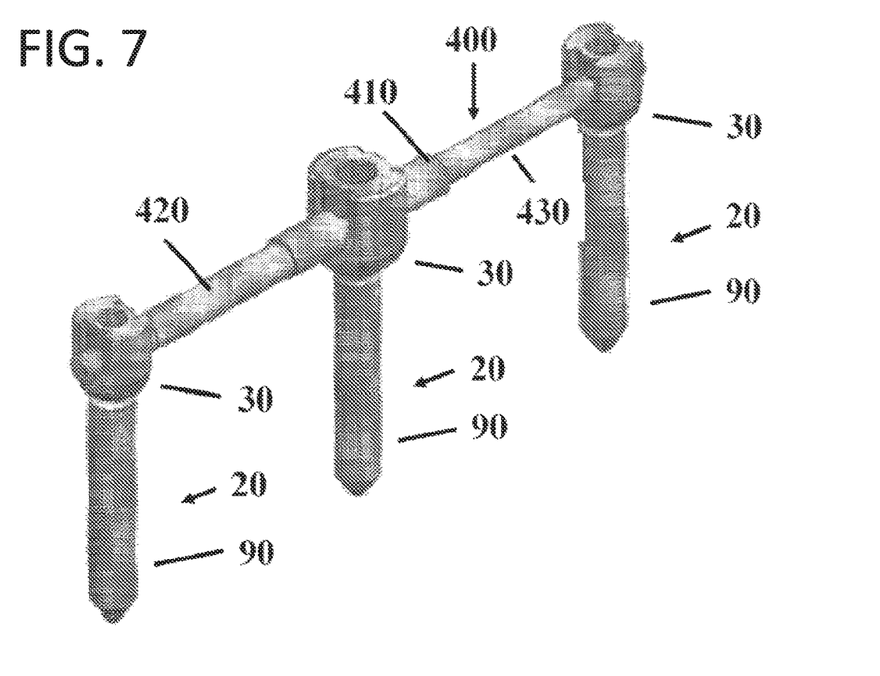
FIG. 7. The embodiment of the system for spinal fixation with a bidirectional telescoping rod shown in FIG. 6, in the extended position.

An alternative embodiment of the system 5 employs a bone anchor 10 with a single rod housing containing a bidirectional telescoping rod 400 to be fastened to the bone anchor 10. The bidirectional telescoping rod is configured to telescope in different directions. This allows the rod 400 to be extended from the first vertebra to two adjacent vertebra (one cranial to the first vertebra and one caudal to the first vertebra) through the same small incision. The alternative embodiment of the system comprises a bone anchor 10 including a bone fastener member 90, a first rod housing 30 comprising a first rod channel 40; a bidirectional telescoping spinal rod 400 positioned within the first rod channel 40, the bidirectional telescoping spinal rod 400 having an extended configuration and a collapsed configuration; wherein the bidirectional telescoping spinal rod 400 extends in two opposite directions from the bone anchor 10. The bidirectional telescoping rod 400 comprises a first elongate member 410 having a cavity 415, a second elongate member 420 configured to fit within the cavity 415, a third 430 elongate member configured to fit within the cavity 415, and an extension mechanism configured to extend the second 420 and third 430 elongate members from the first elongate 410 member in response to a remote signal, such as a rotating magnetic field. The extension mechanism may comprise a rotatable magnet, the rotation of which causes the second 420 and third 430 elongate members to extend.

The system 5 is at least partially composed of a biocompatible non-absorbable material. Specific examples of such suitable materials include titanium, alloys of titanium, steel, and stainless steel. Parts of the system 5 could conceivably be made from non-metallic biocompatible materials, which include aluminum oxide, calcium oxide, calcium phosphate, hydroxyapatite, zirconium oxide, and polymers such as polypropylene.

Figure 5:
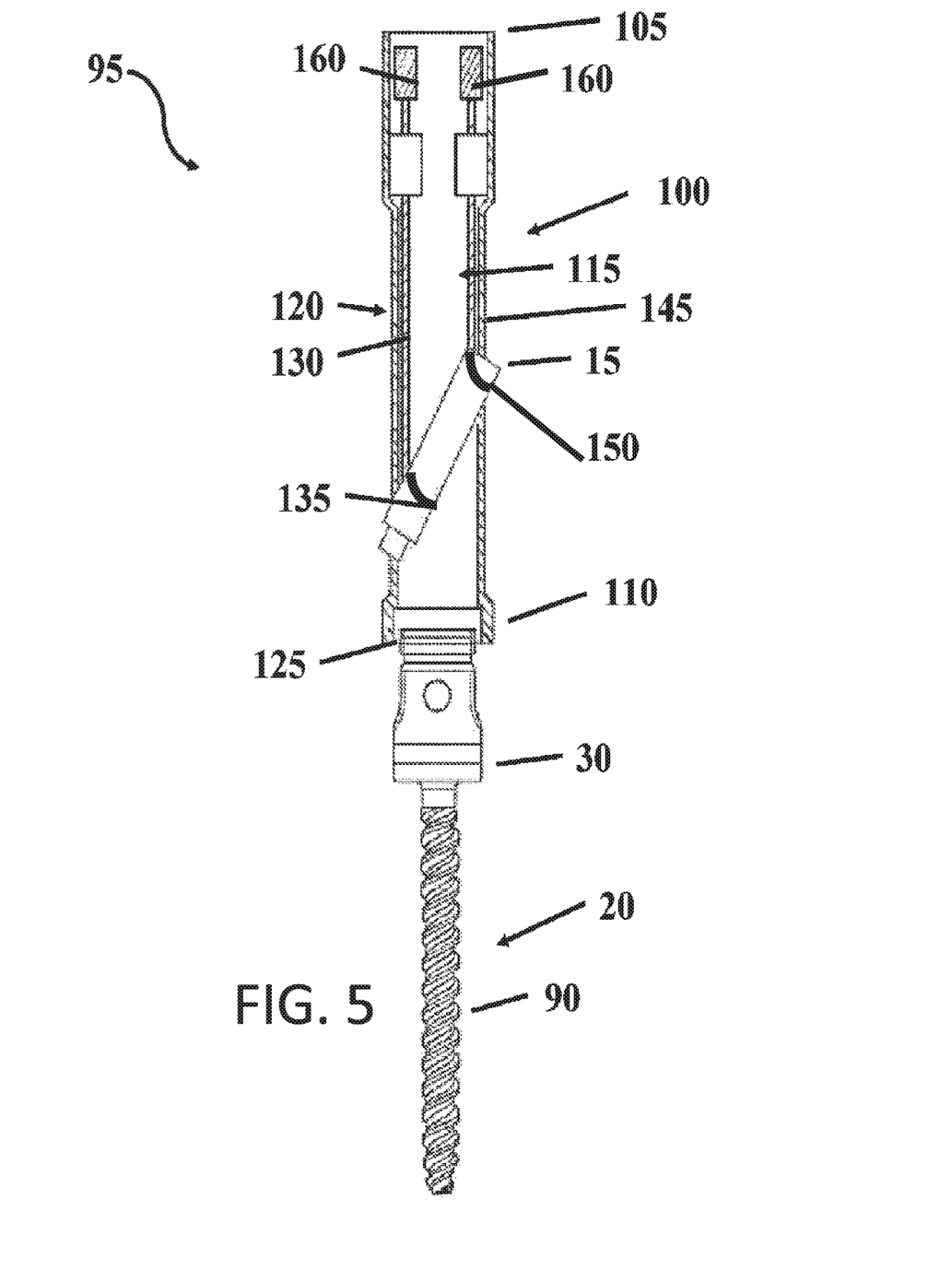
FIG. 5. A side view of an embodiment of the system for spinal fixation in situ, showing guide towers in place holding the telescoping spinal rod.

A guide tower assembly for the inserter-less introduction of a spinal rod is provided. It functions by connecting to a spinal rod at two points, and translating the two points in a distal direction at different velocities. As shown in FIG. 5, a general embodiment of the guide tower 95 comprises an elongate tower member 100 having a proximal end 105, a distal end 110, and a longitudinal axis. A lumen 115 is present within the elongate tower member, running from the proximal end 105 to the distal end 110. A longitudinal slot 120 in the elongate tower member 100 connects the lumen 115 to the exterior of the guide tower 95. A bone anchor engagement member 125 is located at the distal end 110 of the tower member, and is configured to reversibly fasten the elongate tower member 100 to a rod housing 30 of the first bone anchor 10. The spinal rod is held by a first rod holder 130 having a first rod engagement feature 135 at a distal end of the rod holder 130 and a first translating shaft 140 connected to the first rod engagement feature 135, wherein the first translating shaft 140 is capable of translating relative to the elongate tower member 100 parallel to the longitudinal axis of the elongate tower member 100, and wherein the first rod engagement feature 135 translates with the first translating shaft 140; thus the rod can be raised and lowered (i.e., translated proximally or distally) using the translating rod. The guide tower 95 also includes a second rod holder 145 having a second rod engagement feature 150 at a distal end of the second rod holder 145 and a second translating shaft 155 connected to the second engagement feature 150, wherein the second translating shaft 155 is capable of translating relative to the elongate tower member 100 parallel to the longitudinal axis of the elongate tower member 100, wherein the second rod engagement feature 150 translates with the second translating shaft 155. In order to rotate the spinal rod as it is lowered, the second translating shaft 155 is capable of translating at a different velocity than a velocity of translation of the first translating shaft 140.

The lumen 115 in the guide tower assembly 95 is dimensioned to allow the spinal rod to pass through the elongate tower member 100 longitudinally. The longitudinal slot 120 is likewise dimensioned to allow the spinal rod 15 to pass through, and permits the spinal rod to have a length greater than the diameter of the elongate tower member 100. Some embodiments of the guide tower assembly 95 have two longitudinal slots (120a, 120b) in the elongate tower member 100, positioned opposite one another, which allows the spinal rod to protrude from both slots (120a, 120b).

The rod holders (130, 145) keep the rod in place while it is guided into the rod housing 30 of the bone anchor 10. The rod holders (130, 145) may be configured to securely hold the rod before it is seated in the rod channel 40, but to release the rod once the rod is seated. One such embodiment, shown in FIG. 5, is a pincer comprising two semicircular fingers.

In operation, the guide tower assembly 95 functions by lowering each end of the spinal rod at different rates. This can be accomplished by various means. For example, each of the translating shafts (140, 155) may be threaded, with different thread pitches. Thus, when rotated at the same rate, each shaft (140, 155) translates at a different velocity. Rotation of the shafts (140, 155) may be provided by various means, such as by operatively connecting a given shaft to a magnet ("shaft magnet") 160 such that rotation of the shaft magnet 160 causes the threaded shaft (140, 155) to translate parallel to the longitudinal axis of the guide tower 95. The shaft magnet 160 may be mounted to rotate when exposed to a rotating magnetic field. In such embodiments, upon exposure to a rotating magnetic field, one or both of the translating shafts (140, 155) will be caused to translate, possibly at different rates. The shaft magnet 160 may drive rotation of the translating shaft (140, 155), for example if the translating shaft (140, 155) is threaded. The shaft magnet 160 may drive rotation of the translating shaft (140, 155) directly (for example if the shaft magnet 160 is mounted to the shaft (140, 155) in such a way that its axis of rotation is coaxial with the shaft's (140, 155) axis of rotation), or indirectly. In embodiments in which the shaft magnet 160 drives the translating shaft (140, 155) indirectly, it may do so by means of a gear train 85. The shaft magnet 160 may be made of any magnetic material disclosed above as suitable for the rod magnet 45. In some embodiments of the guide tower assembly 95, the rest of the guide tower assembly 95 is made of a non-magnetic material or weakly magnetic material, to prevent interference with the movement of the shaft magnet 160. Specific examples of such nonmagnetic non-absorbable biocompatible material include titanium, alloys of titanium, aluminum oxide, calcium oxide, calcium phosphate, hydroxyapatite, zirconium oxide, and polymers such as polypropylene. Examples of weakly magnetic materials include paramagnetic materials and diamagnetic materials. In a specific embodiment, the weakly magnetic material is austenitic stainless steel.

The utility of the system 5 described above may be enhanced through the use of the guide tower assembly 95. Some embodiments of the guide tower assembly 95 may be specially configured to guide a telescoping spinal rod 15 of the kind described above into position through a small incision. In other embodiments the guide tower is used to guide a conventional spinal rod into position.

A method of fixating a first vertebra to a second vertebra is provided by a minimally invasive approach. A general embodiment of the method comprises fastening a first bone anchor 10 to the first vertebra; fastening a second bone anchor 10 to a second vertebra; inserting a telescoping spinal rod 15 into the first bone anchor 10 in a collapsed configuration; extending the telescoping spinal rod 15 from the collapsed to the extended configuration, to cause the telescoping spinal rod 15 to extend into the second bone anchor 10; locking the telescoping spinal rod 15 in position in the first bone anchor 10; and locking the telescoping spinal rod 15 in position in the second bone anchor 10. Locking may be performed by a variety of methods, such as by inserting a locking screw 165 into the rod housing 30 and tightening it against the rod 15. As discussed above, the telescoping spinal rod 15 has an extended configuration and the collapsed configuration, such that the telescoping spinal rod 15 has a collapsed length that is shorter than a length between the first bone anchor 10 and the second bone anchor 10, and an extended length that is no shorter than the length between the first bone anchor 10 and the second bone anchor 10.

The method may be used with a bone anchor 10 having two rod housings. In that case, the method will further comprise fastening a third bone anchor 10 to a third vertebra; inserting a second telescoping spinal rod 15 into the second rod housing 30 (on the first bone anchor 10) in a collapsed configuration; extending the second telescoping spinal rod 15 from the collapsed to the extended configuration, to cause it to extend into the third bone anchor 10; locking the telescoping spinal rod 15 in position in the second rod housing 30; and locking the telescoping spinal rod 15 in position in the third bone anchor 10.

Figure 4:
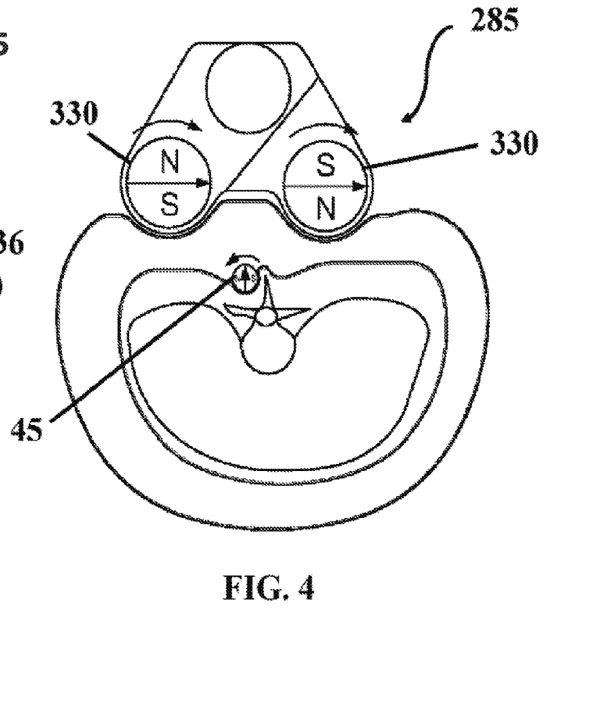
FIG. 4. A transverse cross-sectional view of a subject into whom has been implanted an embodiment of the telescoping spinal rod, showing an embodiment of an external adjustment device positioned to cause the spinal rod to extend or retract.

In some embodiments of the method, the telescoping spinal rod 15 is extended from the collapsed to the extended configuration while said telescoping spinal rod 15 is below the fascia of the subject. Such embodiments of the method have the advantage of connecting two vertebrae without requiring an incision to run between them, as would be required if the spinal rod 15 were implanted while at its full length. In such cases the rod 15 may be configured to extend or contract in response to a remote signal, such as an electromagnetic signal. As described above, one such type of electromagnetic signal is a rotating magnetic field. This may be accomplished using an external rotating magnet 170 or array of magnets, or using an electrically induced magnetic field. One embodiment of the external adjustment device 180 (shown in FIG. 4) is configured for placement on or adjacent to the skin of the subject and includes at least one magnet ("external magnet") 170 configured for rotation. The illustrated embodiment also has a motor 185 configured to rotate the external magnet 170, whereby rotation of the external magnet 170 effectuates rotational movement of the rod magnet 45. As shown in FIG. 4, the external adjustment device 180 may have two external magnets 170. The two external magnets 170 may be configured to rotate at any suitable rate, and in a specific embodiment they are configured to rotate at the same rate. In further embodiments the external magnets 170 are configured to rotate at the same rate such that the positive and negative poles of each external magnet 170 are aligned. Stated another way, in such embodiments the positive ("North") pole of the first external magnet 170 will be at 0° when the positive pole of the second external magnet 170 is at 180°, and the negative ("South") pole of the first external magnet 170 will be at 180° when the negative pole of the second external magnet 170 is at 0°. (Such a configuration is shown in FIG. 4). Because both external magnets 170 rotate in the same direction along parallel axes at the same rate this relative configuration will be preserved through multiple cycles.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 and related laws or otherwise to provide organizational queues. These headings shall not limit or characterize the invention(s) set forth herein.

The invention claimed is:

1. A system for spinal fixation, the system comprising:
   a first bone anchor including
      a distal bone fastener member, and
      a proximal rod housing comprising a first rod channel;
   a first telescoping spinal rod dimensioned to fit within the first rod channel, the first telescoping spinal rod having an extended configuration and a collapsed configuration, wherein the first telescoping spinal rod has a first longitudinal length in the collapsed configuration and a second longitudinal length in the extended configuration, and wherein the first longitudinal length is less than the distance between a vertebral pedicle in a subject and an adjacent vertebral pedicle in the subject; and
   a guide tower assembly for guiding a spinal rod into position from the first bone anchor to a second bone anchor, wherein the guide tower assembly comprises:
      an elongate tower member having a proximal end, a distal end, and a longitudinal axis;
      a lumen running from the proximal end to the distal end of the elongate tower member;
      a longitudinal slot in the elongate tower member that connects to the lumen;
      a bone anchor engagement member at the distal end of the tower member configured to reversibly fasten the elongate tower member to the proximal rod housing of the first bone anchor;
      a first rod holder having a first rod engagement feature at a distal end of the first rod holder and a first translating shaft connected to the first rod engagement feature, wherein the first translating shaft is capable of translating relative to the elongate tower member parallel to the longitudinal axis of the elongate tower member, and wherein the first rod engagement feature translates with the first translating shaft; and
      a second rod holder having a second rod engagement feature at a distal end of the second rod holder and a second translating shaft connected to the second rod engagement feature, wherein the second translating shaft is capable of translating relative to the elongate tower member parallel to the longitudinal axis of the elongate tower member, wherein the second rod engagement feature translates with the second translating shaft and wherein the second translating shaft is capable of translating at a different velocity than a velocity of translation of the first translating shaft.

2. The system of claim 1, wherein the first telescoping spinal rod comprises a rod magnet configured to rotate when exposed to a spinning magnetic field and cause the first telescoping spinal rod to either extend or collapse depending on the direction of rotation of the spinning magnetic field.

3. The system of claim 2, wherein the first telescoping spinal rod comprises:
   a first elongate element containing a cavity;
   a second elongate element dimensioned to at least partially fit within the cavity; and
   a lead screw coupled to rotate when the rod magnet rotates, and comprising an externally threaded region, such that rotation of the lead screw causes the second elongate element to translate relative to the first elongate element.

4. The system of claim 1, wherein the second longitudinal length is no less than the distance between the vertebral pedicle in a subject and an adjacent vertebral pedicle in the subject.

5. The system of claim 1, configured to allow the first telescoping spinal rod to be inserted towards the first bone anchor with an axis of the first telescoping spinal rod generally parallel to the guide tower assembly and reoriented to a position with the axis of the first telescoping spinal rod generally perpendicular to the guide tower assembly prior to adjusting the first telescoping spinal rod to the extended position, the distal end of the first spinal telescoping rod passing through the longitudinal slot and underneath the fascia.

6. The system of claim 1, configured to allow the first telescoping spinal rod to be coupled directly to the guide tower assembly for insertion without an inserter.

7. The system of claim 1, wherein at least one of the first translating shaft and the second translating shaft is a threaded shaft operatively connected to a first shaft magnet, such that rotation of the first shaft magnet causes the threaded shaft to translate.

8. The system of claim 1, wherein
   the first translating shaft is a threaded shaft operatively connected to a first shaft magnet, such that rotation of the first shaft magnet causes the first threaded shaft to translate parallel to the longitudinal axis of the guide tower; and
   the second translating shaft is a threaded shaft operatively connected to a second magnet, such that rotation of the second magnet causes the second threaded shaft to translate parallel to the longitudinal axis of the guide tower.

9. The system of claim 8, wherein the first shaft magnet and the second magnet are rotatably mounted to rotate when exposed to a rotating magnetic field, and wherein the thread pitch of the first threaded shaft does not equal the thread pitch of the second threaded shaft.

10. The system of claim 1, wherein the first and second rod engagement features are configured to engage the rod until the rod is seated in the first bone anchor.

11. The system of claim 1, wherein the longitudinal slot has a circumferential width sufficient to admit a spinal rod.

12. A system for spinal fixation, the system comprising:
a first bone anchor comprising a distal bone fastener member, and a proximal rod housing comprising a first rod channel;
a first telescoping spinal rod dimensioned to fit within the first rod channel, the first telescoping spinal rod having an extended configuration and a collapsed configuration, wherein the first telescoping spinal rod has a first longitudinal length in the collapsed configuration and a second longitudinal length in the extended configuration, and wherein the first longitudinal length is less than the distance between a vertebral pedicle in a subject and an adjacent vertebral pedicle in the subject; and
a guide tower assembly for guiding a spinal rod into position from the first bone anchor to a second bone anchor, the guide tower assembly comprising:
an elongate tower member having a proximal end, a distal end, and a longitudinal axis;
a first rod holder having a first rod engagement feature at a distal end of the first rod holder and a first translating shaft connected to the first rod engagement feature, wherein the first translating shaft is capable of translating relative to the elongate tower member parallel to the longitudinal axis of the elongate tower member, and wherein the first rod engagement feature translates with the first translating shaft; and
a second rod holder having a second rod engagement feature at a distal end of the second rod holder and a second translating shaft connected to the second rod engagement feature, wherein the second translating shaft is capable of translating relative to the elongate tower member parallel to the longitudinal axis of the elongate tower member, wherein the second rod engagement feature translates with the second translating shaft and wherein the second translating shaft is capable of translating at a different velocity than a velocity of translation of the first translating shaft.

13. The system of claim 12, wherein the guide tower member further comprises:
a lumen running from the proximal end to the distal end of the elongate tower member.

14. The system of claim 13, wherein the guide tower member further comprises:
a longitudinal slot in the elongate tower member that connects to the lumen.

15. The system of claim 12, wherein the guide tower member comprises:
a bone anchor engagement member at the distal end of the tower member configured to reversibly fasten the elongate tower member to the proximal rod housing of the first bone anchor.

16. The system of claim 12, wherein at least one of the first translating shaft and the second translating shaft is a threaded shaft operatively connected to a first shaft magnet, such that rotation of the first shaft magnet causes the threaded shaft to translate.

17. The system of claim 12, wherein
the first translating shaft is a threaded shaft operatively connected to a first shaft magnet, such that rotation of the first shaft magnet causes the first threaded shaft to translate parallel to the longitudinal axis of the guide tower; and
the second translating shaft is a threaded shaft operatively connected to a second magnet, such that rotation of the second magnet causes the second threaded shaft to translate parallel to the longitudinal axis of the guide tower.

18. The system of claim 17, wherein the first shaft magnet and the second magnet are rotatably mounted to rotate when exposed to a rotating magnetic field.

19. The system of claim 18, wherein the thread pitch of the first threaded shaft does not equal the thread pitch of the second threaded shaft.

20. The system of claim 12, wherein the first telescoping spinal rod comprises a rod magnet configured to rotate when exposed to a spinning magnetic field and cause the first telescoping spinal rod to either extend or collapse depending on the direction of rotation of the spinning magnetic field.

21. The system of claim 20, wherein the first telescoping spinal rod comprises:
a first elongate element containing a cavity;
a second elongate element dimensioned to at least partially fit within the cavity; and
a lead screw coupled to rotate when the rod magnet rotates, and comprising an externally threaded region, such that rotation of the lead screw causes the second elongate element to translate relative to the first elongate element.

* * * * *